United States Patent [19]

Hargreaves, II et al.

[11] 4,215,078
[45] Jul. 29, 1980

[54] PROCESS FOR MANUFACTURING CHLOROPRENE AND 2,3-DICHLOROBUTADIENE-1,3

[75] Inventors: Chester A. Hargreaves, II, Wilmington, Del.; Alexander T. Harris, Metairie, La.; Robert A. Schulze, Wilmington, Del.

[73] Assignee: E. I. Du Pont de Nemours and Company, Wilmington, Del.

[21] Appl. No.: 26,202

[22] Filed: Apr. 2, 1979

[51] Int. Cl.$^2$ .............................................. C07C 21/20
[52] U.S. Cl. ................................ 260/655; 260/654 D
[58] Field of Search ........................... 260/654 D, 655

[56] References Cited

U.S. PATENT DOCUMENTS

| | | | |
|---|---|---|---|
| 2,539,307 | 1/1951 | Koll | 260/656 |
| 2,999,888 | 9/1961 | Crocker | 260/655 |
| 3,188,357 | 6/1965 | Blumbergs | 260/655 |
| 3,639,492 | 2/1972 | Campbell | 260/655 |
| 3,639,493 | 2/1972 | Campbell | 260/655 |
| 3,754,044 | 8/1973 | Hargreaves et al. | 260/655 |
| 3,876,716 | 4/1975 | Campbell | 260/655 |
| 3,936,508 | 2/1976 | Wenzel et al. | 260/655 |
| 3,965,203 | 6/1976 | Smith | 260/655 |
| 3,981,937 | 9/1976 | Campbell et al. | 260/655 |

Primary Examiner—C. Davis

[57] ABSTRACT

An improved process for the production of chloroprene, which is the critical monomer constituent of neoprene rubbers, and of 2,3-dichlorobutadiene-1,3, which often is copolymerized with chloroprene to provide better low temperature properties of the resulting elastomer, involves dehydrochlorination of a chlorinated hydrocarbon such as 3,4-dichlorobutene-1, 2,3,4-trichlorobutene-1, or 1,2,3,4-tetrachlorobutane, with an aqueous mixture of sodium hydroxide and sodium chloride having the composition of chlor/alkali cell liquor; separation of the organic phase from which the desired product, chloroprene or 2,3-dichlorobutadiene-1,3, is recovered by distillation; and recirculation of the aqueous (brine) phase to the electrolysis apparatus, from which the sodium hydroxide-sodium chloride liquor is returned to the dehydrochlorination step. This process saves energy in that it does not require cell liquor concentration to isolate pure sodium hydroxide, and it is environmentally desirable because it avoids problems associated with brine disposal.

8 Claims, 1 Drawing Figure

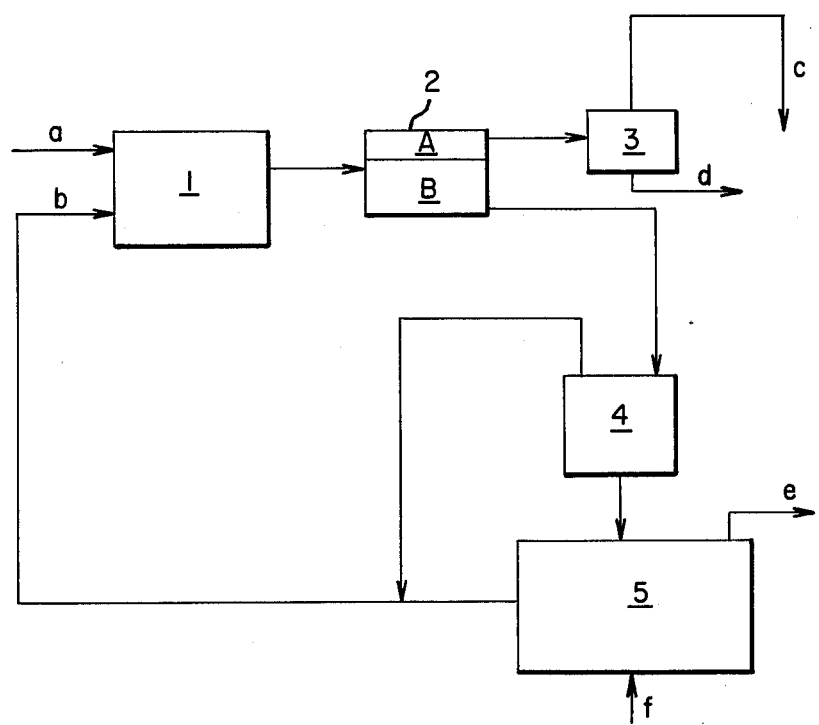

PROCESS FOR MANUFACTURING CHLOROPRENE AND 2,3-DICHLOROBUTADIENE-1,3

BACKGROUND OF THE INVENTION

This invention is directed to an improved process for the production of chloroprene (2-chlorobutadiene-1,3) by the dehydrochlorination of 3,4-dichlorobutene-1 and production of 2,3-dichlorobutadiene-1,3 by the dehydrochlorination of 2,3,4-trichlorobutene-1 or 1,2,3,4-tetrachlorobutane with aqueous sodium hydroxide.

According to most prior art processes, this dehydrochlorination is carried out with a solution of caustic soda at a temperature up to about 100° C. or even higher. Chloroprene or 2,3-dichlorobutadiene-1,3, as the case may be, is removed from the crude reaction mixture by any convenient method, such as ordinary distillation, steam distillation, or phase decantation. The crude brine left behind can be disposed of, for example, by being pumped into wells from which it gradually seeps into the ground or by being injected into fresh or salt water streams. Because about 3 kg of brine are produced for each kg of chloroprene, and even larger amounts of brine are produced in the manufacture of 2,3-dichlorobutadiene-1,3, brine disposal is a serious problem, both from the standpoint of cost involved and environmental hazard created.

SUMMARY OF THE INVENTION

According to the present invention, there is now provided an improved process for the production of chloroprene by the dehydrochlorination of 3,4-dichlorobutene-1 and production of 2,3-dichlorobutadiene-1,3 by the dehydrochlorination of 2,3,4-trichlorobutene-1 or of 1,2,3,4-tetrachlorobutane, the process being characterized by that the dehydrochlorination is carried out with an aqueous solution of a mixture of sodium hydroxide and sodium chloride having the composition of chlor/alkali cell liquor; the reaction product mixture is separated into an organic phase and an aqueous phase; the desired product, chloroprene or 2,3-dichlorobutadiene-1,3, is recovered from the organic phase; and the aqueous phase, consisting essentially of sodium chloride brine, is electrolyzed to give an aqueous solution of a mixture of sodium hydroxide and sodium chloride, which is recycled to the dehydrochlorination step.

BRIEF DESCRIPTION OF THE DRAWING

The drawing represents a schematic flowsheet of one preferred embodiment of the process of the present invention for making chloroprene.

DETAILED DESCRIPTION OF THE INVENTION

While it has been heretofore customary in the industry to use sodium hydroxide solutions for the dehydrochlorination of 3,4-dichlorobutene-1, 2, 3, 4-trichlorobutene-1, and 1,2,3,4-tetrachlorobutane, the present invention calls for the use of chlor/alkali cell (brine electrolysis cell) liquor. A typical cell liquor is an aqueous solution of about 6–12% sodium hydroxide and 10–18% of sodium chloride. These concentrations may vary considerably, depending on the degree of electrolysis. Naturally, sodium hydroxide contained in the cell liquor is the active ingredient. Sodium chloride is inert under the conditions of the dehydrochlorination reaction.

The dehydrochlorination reaction is preferably carried out in the presence of a suitable catalyst. The preferred catalysts are quaternary ammonium compounds, and especially quaternary ammonium chlorides, for example, those described in U.S. Pat. No. 3,981,937 to Campbell et al. Other useful catalysts are quaternary phosphonium compounds, for example, those described in U.S. Pat. No. 3,639,493 to Campbell; sulfonium compounds, such as those disclosed in U.S. Pat. No. 3,639,492 to Campbell; amine oxides, such as those disclosed in U.S. Pat. No. 3,876,716 to Campbell; and monoor diphosphate esters in which the ester group is an alkoxy- or alkylphenoxy poly(alkyleneoxy) radical, the number of alkyleneoxy groups being about 2–20, and alkylene being ethylene or propylene. These catalysts can be used either alone, in an amount of about 0.01–10% (0.05 to 15% in the case of phosphate esters) based on the weight of the starting chlorinated hydrocarbon, as shown in Canadian Pat. No. 834,780 to the Du Pont Company, or in the presence of a promoter, as described in U.S. Pat. No. 3,754,044 to Hargreaves et al. The amount of promoter usually is about 0.05–1% based on the starting chlorinated hydrocarbon. Typical quaternary ammonium chlorides include, for example, various (alkyl) (benzyl) (2-propanol) ammonium chlorides and (alkylbenzyl) (2-propanol) ammonium chlorides in which the number of 2-propanol groups may vary from 1 to 3. Typical quaternary phosphonium compounds are, for example, tetrabutylphosphonium chloride, benzyldimethyl(3,5,5-trimethylhexyl)phosphonium benzenesulfonate, and (2-hydroxyethyl)tricyclohexylphosphonium chloride. Representative sulfonium compounds are (dihexyl) (methyl) sulfonium iodide, (dodecyl) (ethyl) (methyl)sulfonium chloride, and 1,6-hexamethylenebis(dimethylsulfonium bromide). Examples of amine oxides include diethyl(2-oleoylaminoethyl)amine oxide, (dodecylaminocarbonylmethyl)amine oxide, and N-alkylmorpholine N-oxide in which the alkyl groups are derived from coconut oil. For a more complete listing of suitable catalysts one should consult U.S. Pat. Nos. 3,981,937; 3,639,492; 3,639,493; 3,876,716; and 3,754,044, and Canadian Pat. No. 834,780, which are incorporated herein by reference. In the presence of the above catalysts it is possible to carry out the dehydrochlorination reaction at moderate temperatures, e.g., below 70° C. It is preferred to operate at a temperature not over 65° C., to avoid undesirable side reactions. However, the temperature of the dehydrochlorination step is not critical.

It is recognized that at higher operating temperatures, especially in the absence of catalysts, and when the residence time is excessively long, the proportion of the side-products, especially of high-boiling highly chlorinated materials, will increase. Organic contaminants always will be present in the brine formed in the dehydrochlorination step, whatever phase separation method is used. These high-boiling organic contaminants tend to be scavenged by the semi-permeable membrane separating the anode from the cathode in the cell in which brine is subsequently electrolyzed and with time cause clogging of the membrane. It has been found experimentally that brine containing about 100 ppm or less of total organic carbon (hereafter, TOC) can be electrolyzed in commercial cells for periods of several months without excessive membrane clogging. As the TOC in the brine increases, however, the useful life of the membrane decreases. It is important that the proportion of organic nitrogen in the brine (for example, derived from the dehydrochlorination catalyst) be very small, e.g. less than 1 ppm. This low concentration will normally be inherently obtained in the usual phase separation techniques. The brine should contain no suspended solids, such as NaCl, since they would foul up the electrodes. If solids are present, they should be removed prior to electrolysis, for example, by filtration or by addition of water in sufficient amount to dissolve NaCl.

Referring now to the drawing, the dehydrochlorination step takes place in reactor 1. 3,4-Dichlorobutene-1 is introduced through line a, and a sodium hydroxide/sodium chloride solution is introduced through line b. If a catalyst is used, it can be premixed either with the NaOH/NaCl solution or with 3,4-dichlorobutene-1; or it can be introduced separately.

In the operation of the process of this invention, the mole ratio of sodium hydroxide to 3,4-dichlorobutene-1 in reactor 1 can vary from about 0.5:1 to 20:1, although an excess of sodium hydroxide is preferred. A nearly equimolar ratio can be used with the more active catalysts. It is advisable to operate in the absence of oxygen and in the presence of conventional polymerization inhibitors, for example, phenothiazine, p-nitrosodiphenylamine, diisobutyl nitrosate, 4-tert-butylpyrocatechol, 2,6-di-tert-butyl-p-cresol, or a dialkylhydroxylamine. Usually one inhibitor soluble in the organic phase and one soluble in the water phase will both be present. The manner of using such inhibitors is well known to the art. The reaction temperature is above 0° C., preferably above 40° C. The process can be carried out either continuously or batchwise. If the reaction is catalyzed, short residence times are sufficient to achieve nearly full conversion. According to this preferred embodiment, the crude reaction mixture, following the dehydrochlorination step, is phase-decanted in decanter 2. The organic phase forms the upper layer A and the aqueous phase the lower layer B. Because clean separation of phases is important, it is advisable to adjust the type and amount of dehydrochlorination catalyst in reactor 1 in such a way that excessive emulsification does not occur at the phase interface. Preferably, decanter 2 is maintained at the same temperature as reactor 1. The organic phase, to which additional polymerization inhibitors may be added, is distilled in vessel 3 at a reduced pressure to yield pure chloroprene which is removed from the top through line c. The high boiling residue containing the catalyst is removed from the bottom through line d and disposed of, preferably by incineration.

Of course, any other method of phase separation, including extraction, steam distillation, centrifugation, etc., can be used, instead of ordinary phase decantation.

The aqueous phase, which contains approximately 22% NaCl and 1% NaOH is introduced into evaporator 4 maintained at about 65° C. and a pressure of 12 kPa. Most of the organic materials dissolved or dispersed in the aqueous phase and some water are flash-stripped at this stage and returned to reactor 1. A small higher-boiling fraction of organic compounds will still remain dispersed in the brine, but it usually is not over 100 ppm. Brine containing higher levels of organic materials may be further purified, if desired, e.g., by extraction. Various electrolyte processes for manufacturing sodium hydroxide are described, among others, in Kirk-Othmer's Encyclopedia of Chemical Technology, 2nd Ed., Vol. 1, 1963, pp. 678–687. Brine is electrolyzed in cell 5; chlorine is removed through line e and the cell liquor is pumped to reactor 1 to be used in the dehydrohalogenation step of this process. Make-up sodium chloride solution in water can be added to the chlor/alkali cell 5 through line f.

Because in the present process the brine is reused and does not have to be disposed of by pumping it into wells or into bodies of water, an important ecological benefit is realized. It is realized that the amount of chloroprene that can be obtained per unit of time in a given reactor will be smaller than when sodium hydroxide alone is used since a more concentrated sodium hydroxide solution can then be used. However, in order to obtain those more concentrated sodium hydroxide solutions, it is necessary to concentrate the cell liquor sufficiently to cause sodium chloride to precipitate out of the solution. This precipitated sodium chloride is then removed by filtration or decantation, and the concentrated mother liquor either is used as such or is rediluted. The evaporation of cell liquor must be carried out in expensive nickel equipment and requires a large amount of energy. Thus, the present process also provides a considerable energy saving and requires lower capital investment since the cell liquor-concentration step is eliminated. The penalty of lower output is more than compensated by a reduced operating cost. It can be seen readily that the present invention satisfies modern industrial needs.

This invention is now illustrated by the following examples of certain representative embodiments thereof, where all parts, proportions and percentages are by weight unless otherwise indicated. The catalyst was (coco)bis($\beta$-hydroxypropyl) (benzyl) ammonium chloride. Total organic carbon is abbreviated as TOC.

EXAMPLE 1

A sample of chlor/alkali cell liquor obtained from a commercial source containing 8.4% of NaOH and 18.2% NaCl was diluted with water so that the sodium hydroxide concentration was 5.2%.

Eight hundred and thirty-two grams of the diluted liquor was used to dehydrochlorinate 189 g of 3,4-dichlorobutene-1 in the presence of 0.447 g of the catalyst at 50±1° C., to yield chloroprene at 90.5% conversion is 60 minutes.

EXAMPLE 2

Chloroprene was prepared by the low temperature catalytic process of U.S. Pat. No. 3,981,937. The waste brine was separated by two different techniques. The first involved steam stripping at 90° C. TOC content in the brine was 250 ppm. The second involved decantation followed by vacuum stripping of volatile organic compounds at 65° C., and 12.0 kPa. The TOC content was 82 ppm.

EXAMPLE 3

Waste brine containing 82 ppm TOC from Example 2 was successfully electrolyzed in standard equipment using a diaphragm chlor/alkali cell to produce cell liquor containing 11.5% NaOH and 14.5% NaCl which was subsequently used to produce chloroprene according to the technique of Example 1.

I claim:

1. In a process for the dehydrochlorination of 3,4-dichlorobutene-1 to chloroprene or of 2,3,4-trichlorobutene-1 or 1,2,3,4-tetrachlorobutane to 2,3-dichlorobutadiene-1,3, the improvement of carrying out the dehydrochlorination with an aqueous solution of a mixture of sodium hydroxide and sodium chloride having the composition of chlor/alkali cell liquor; separating the reaction product mixture into an organic phase and an aqueous phase; recovering the desired product, chloroprene or 2,3-dichlorobutadiene-1,3, from the organic phase; electrolyzing the aqueous phase, consisting essentially of sodium chloride brine, in a chlor/alkali cell to a liquor consisting essentially of an aqueous solution of a mixture of sodium hydroxide and sodium chloride; and recycling the chlor/alkali cell liquor to the dehydrochlorination step.

2. The process of claim 1 wherein the dehydrochlorination step is carried out at a temperature not exceeding 70° C.

3. The process of claim 2 wherein the temperature of the dehydrochlorination step is at most 65° C.

4. The process of claim 2, in which a catalyst is used in the dehydrochlorination step.

5. The process of claim 4 wherein the catalyst is a quaternary ammonium, a quaternary phosphonium, or a sulfonium compond.

6. The process of claim 1 wherein the organic phase and the aqueous phase are separated by phase decantation following the dehydrochlorination step.

7. The process of claim 6 wherein the temperature of the liquids in the decantation step is substantially the same as the temperature in the dehydrochlorination step.

8. The process of claim 1 wherein the total organic carbon content of the brine being electrolyzed in the chlor/alkali cell step is less than about 100 ppm.

* * * * *